United States Patent [19]
Chromecek

[11] 3,966,902

[45] June 29, 1976

[54] POLYMER COMPLEX CARRIERS FOR AN ACTIVE INGREDIENT

[75] Inventor: Richard C. Chromecek, Goshen, Conn.

[73] Assignee: Airwick Industries, Inc., Carlstadt, N.J.

[22] Filed: Mar. 14, 1975

[21] Appl. No.: 558,345

Related U.S. Application Data

[63] Continuation-in-part of Ser. No. 252,823, May 21, 1972, Pat. No. 3,886,125.

[52] U.S. Cl. .................................. 424/59; 8/10.1; 252/522; 252/108; 252/302; 252/351; 424/39; 424/60; 424/66; 424/67; 424/68; 424/76; 424/78; 424/81; 424/167; 424/168; 424/186; 424/219; 424/224; 424/285; 424/306; 424/324; 424/DIG. 8; 424/DIG. 10

[51] Int. Cl.$^2$ ...................... A61K 7/44; A61K 7/46; A61K 31/78

[58] Field of Search ............... 260/78.3 UA, 78.5 B; 424/59, 78, 81, DIG. 8, DIG. 10, 66, 67, 68; 252/522

[56] References Cited

UNITED STATES PATENTS 3,576,760   4/1971   Gould et al. ...................... 252/403

*Primary Examiner*—John Kight, III
*Attorney, Agent, or Firm*—Curtis, Morris & Safford

[57] ABSTRACT

Compositions comprising an effective amount of an active ingredient such as a medicinal agent, disinfectant, pesticide, insect repellant, or a cosmetic agent such as an antiperspirant, a bath oil, a fragrance, sunscreen, soap, hair dye, tanning agent, etc., in a carrier comprising a polymer comprising a monomer having hydrophilic functional groups such as hydroxyl, carboxyl, or amino groups and containing aluminum, zinc, or zirconium bound in complex form.

12 Claims, No Drawings

POLYMER COMPLEX CARRIERS FOR AN ACTIVE INGREDIENT

This application is a continuation-in-part of pending application Ser. No. 252,823 filed May 21, 1972, now U.S. Pat. No. 3,886,125.

The present invention relates to compositions comprising a polymer complex carrier and an active ingredient entrapped therein. More in particular, this invention relates to compositions wherein the polymer complex carrier is a polymer formed at least in part from a monomer having hydrophilic functional groups such as hydroxyl and/or carboxyl and/or amino groups and containing alumninum, zinc or zirconium metal bound in complex form. The polymer complexes are particularly suitable for use as carriers for active ingredients such as medicinal agents, fragrances, insecticides, pesticides, herbicides, etc.

Complexes of aluminum with low molecular weight organic compounds containing hydroxyl groups are already known. Thus, it has already been proposed to use propylene glycol, low molecular weight ethylene glycol homologs such as for instance, di-, tri-, and tetra-ethylene glycol, hydroxy acids such as for example, lactic, tartaric, gluconic and glycolic acids, for complexing aluminum chlorohydrol. The resulting complexes are soluble in ethyl alcohol and do not precipitate out aluminum hydroxide over a wide pH range embracing pH values of 1 to 11. It is necessary, however, that such complexes contain a limited amount of water in order for them to possess the indicated solubility in ethyl alcohol. As a matter of fact, as a condition for such solubility two hydroxyl groups are required to be present in the low molecular weight organic compound.

It is also known to produce hydrophilic polymers and copolymers having certain desirable physical, optical and physiological properties.

These hydrophilic polymers or hydrogels retain a large percentage of water relative to the weight of their dry substance. In their hydrated condition they are elastically deformable under relatively small pressure but virtually immune to plastic deformation. They may be colorless and also may be optically clear. They form semi-permeable membranes which permit passage of water and certain dissolved materials but retain others. When the aqueous constituent of the hydrogel is of a composition similar or analogous to that of physiological saline, the hydrogels are compatible with body tissue for extended periods and may be employed for implants in the body or for objects to be used in contact with mucous membranes such as contact lenses. They constitute a class of valuable soluble or swellable polymers.

In accordance with the invention, it has now been found that polymer complexes composed at least in part of a polymer containing hydrophilic functional groups and containing aluminum, zinc or zirconium metal bound in complex form and having entirely novel properties can be prepared by reacting such a polymer or copolymer or the precursor monomer or monomers during the polymerization thereof with an aluminum, zinc or zirconium salt, i.e., by contacting the reaction mixture containing the functional group containing monomer, polymer or copolymer with the salt of the metal sought to be complexed.

Starting monomer materials which may be utilized in accordance with the present invention are preferably hydroxy alkyl esters of alpha, beta-unsaturated carboxylic acids such as 2-hydroxy ethylacrylate or methacrylate, hydroxypropylacrylate or methacrylate and the like. Many derivatives of acrylic or methacrylic acid other than the esters mentioned are also suitable as starting monomer materials for use in the forming of the hydrophilic polymers. These include, but are not limited to the following monomers: dimethylaminoethyl methacrylate, piperidinoethyl methacrylate, morpholinoethyl methacrylate, methacrylylglycolic acid, methacrylic acid as such, the monomethacrylates of glycol, glycerol, and of other polyhydric alcohols, the monomethacrylates of dialkylene glycols and polyalkylene glycols, and the like. The corresponding acrylates in each instance may be substituted for the methacrylates.

Examples of hydrophilic monomers preferred for use as starting materials in accordance with the invention include the following: 2-hydroxyethyl acrylate or methacrylate, diethylene glycol acrylate or methacrylate, 2-hydroxypropyl acrylate or methacrylate, 3-hydroxypropyl acrylate or methacrylate, tetraethyleneglycol acrylate or methacrylate, pentaethyleneglycol acrylate or methacrylate, dipropyleneglycol acrylate or methacrylate, acrylamide, methacrylamide, diacetone acrylamide methylolacrylamide, methylolmethacrylanide and the like.

Examples of hydrophilic monomers containing carboxylic acid groups as functional groups and suitable for use as starting materials in accordance with the invention include the following: acrylic acid, methacrylic acid, itaconic acid, aconitic acid, cinnamic acid, crotonic acid, mesaconic acid, maleic acid, fumaric acid and the like.

Partial esters of the above acids are also suitable for use as starting monomer materials in accordance with the invention. Instances of such esters are the following: mono-2-hydroxypropyl aconitate, mono-2-hydroxyethyl maleate, mono-2-hydroxypropyl fumarate, mono-ethyl itaconate, monomethyl cellosolve ester of itaconic acid, monomethyl cellosolve ester of maleic acid, and the like.

Instances of suitable hydrophilic monomers containing amino groups as functional groups include the following: diethylaminoethyl acrylate or methacrylate, dimethylaminoethyl acrylate or methacrylate, monoethylaminoethyl acrylate or methacrylate, tert. butylaminoethyl methacrylate, para-amino styrene, ortho-amino styrene, 2-amino-4-vinyl toluene, piperidinoethyl methacrylate, morpholinoethyl methacrylate, 2-vinyl pyridine, 3-vinyl pyridine, 4-vinyl pyridine, 2-ethyl-5-vinyl pyridine, dimethylaminopropyl acrylate and methacrylate, dimethylaminoethyl vinyl ether, dimethylaminoethyl vinyl sulfide, diethylaminoethyl vinyl ether, amonoethyl vinyl ether, 2-pyrrolidinoethyl methacrylate, 3-dimethylaminoethyl-2-hydroxy-propyl acrylate or methacrylate, 2-aminoethyl acrylate or methacrylate, isopropyl methacrylamide, N-methyl acrylamide or methacrylamide, 2-hydroxyethyl acrylamide or methacrylamide, 1-methacryloyl-2-hydroxy-3-trimethyl ammonium chloride or sulfomethylate, 2-(1-aziridinyl)-ethyl methacrylate, and the like.

A portion of the monomer or monomers having the complex forming groups can be replaced by a monomer or monomers which do not contain any complex forming group such as styrene, vinyl acetate, vinyl chloride, vinylidene chloride, alkyl acrylates, alkyl methacrylates, alkoxyalkyl acrylates, alkoxyalkyl methacrylates, halogenalkyl acrylates, halogenalkyl methacrylates, cyano acrylates and methacrylates, acrylonitrile, vinylbenzoate, and the like.

It has also been found that a part of the polymeric system can be derived from a monomer or monomers having quaternary ammonium sulfonic acid or thio groups or aldehyde groups.

By appropriate choice of the starting monomers and also of the concentration of the monomer in the reaction mixture, polymers having a very broad range of physical and chemical properties may be obtained. These properties may be further varied by altering the ratio between the monofunctional and polyfunctional monomers particularly as to the solubility and swelling capacity of the resultant polymeric materials.

As is evident from the illustrations given of suitable monomeric reactants, only one type of functional group, i.e., hydroxy, carboxylic acid or amino group is required to be present, is sufficient for formation of the desired complex to take place.

Starting metal salts for forming the complex include aluminum, zirconium and zinc salts, such as for instance, aluminum chlorohydrol, aluminum dichlorohydrol, aluminum bromohydrol, aluminum trichloride, the hydrates of aluminum trichloride such as $Al_2OHCl_5$, $Al_2(OH)_2Cl_4$, up to and including $Al_2(OH)_5Cl$ and $Al(OH)_3$, zinc chlorohydrol, zinc bromohydrol, zinc chloride, zirconium chlorohydrol, zirconium chloride, aluminum bromide, aluminum bromohydride, aluminum sulfate, aluminum sulfamate and the corresponding hydrates thereof. Instances of preferred compounds for use in forming the complex copolymers are the aluminum salts and in particular, aluminum chlorohydrol and aluminum bromohydrol.

The aluminum salt can be introduced into the reaction mixture either as a solid or in the form of its aqueous, aqueous-alcoholic or other suitable system.

The amount of aluminum salt required to be used with respect to the reactive monomer groups can be varied over a relatively wide range. Generally, the amount of aluminum salt which is required to be present in the monomer aluminum salt complex for a satisfactory product to be obtained amounts to 0.1–10.0 mole percent. Up to 50 mole percent of aluminum salt can, however, be bound in complex form to the monomer units. It is possible, however, for even higher amounts of the aluminum salt to be bound to the monomeric units because of the polymeric nature of the basic aluminum salts. Thus, up to 90 mole percent of aluminum salt can be complexed. However, the amount of salt between 50–90 mole percent is bound in a relatively weak form and can be readily split off by reaction with water. Nevertheless, films formed of complex polymer having 80–90 mole percent of aluminum salt are entirely clear, without any evidence that crystallization of the salt has taken place.

Hereinafter, whenever reference is made to the terms "aluminum complex", "aluminum salt", etc., it is to be understood that while aluminum is preferred, the other metal complexes may be similarly prepared using the corresponding metal salt and these would have substantially the same properties as the aluminum complex.

The novel polymer complexes according to the invention can be prepared by reacting the monomer or monomers with an aluminum salt prior to the polymerization thereof. The resultant complex monomers are thereafter polymerized in the conventional manner. The monomer complex formation can also be carried out in the presence of additional non-complex forming monomers.

When the polymerization is carried out in the presence of a radical forming catalyst utilizing the bulk polymerization technique, hard brittle polymers are generally formed.

When the starting hydrophilic monomer is polymerized with a crosslinking agent, three-dimensional insoluble polymers are formed. Preferred crosslinking agents in this connection are the diesters of acrylic or methacrylic acid with a bifunctional alcohol which has at least two esterifiable hydroxy groups. The diesters just mentioned may be replaced by other crosslinking agents of which the following are merely illustrative. Ethyleneglycol diacrylate or dimethacrylate, 1,2-butyleneglycol diacrylate or dimethacrylate, 1,3-butyleneglycol diacrylate or dimethacrylate, 1,4-butyleneglycol diacrylate or dimethacrylate, propyleneglycol diacrylate or dimethacrylate, diethyleneglycol diacrylate or dimethacrylate, dipropyleneglycol diacrylate or dimethacrylate, divinyl benzene, divinyl toluene, diallyl tartrate, allyl pyruvate, allyl maleate, divinyl tartrate, triallyl melamine, N,N'-methylene bis acrylamide, glycerine dimethacrylate, glycerine trimethacrylate, diallyl maleate, divinyl ether, diallyl monoethyleneglycol citrate, ethyleneglycol vinyl allyl citrate, allyl vinyl maleate, diallyl itaconate, ethyleneglycol diester of itaconic acid, divinyl sulfone, hexahydro 1,3,5-triacyltriazine, triallyl phosphite, diallyl ether of benzene phosphonic acid, maleic anhydride triethylene glycol polyester, polyallyl sucrose, polyallyl glucose, sucrose diacrylate, glucose dimethacrylate, pentaerythritol di-, tri- & -tetraacrylate or methacrylate, trimethylol propane di- and triacrylate or methacrylate, sorbitol dimethacrylate, 2-(1-aziridinyl)-ethyl methacrylate, tri-ethanolamine diacrylate or dimethacrylate, triethanolamine triacrylate or trimethacrylate, tartaric acid dimethacrylate, triethyleneglycol dimethacrylate, the dimethacrylate of bis-hydroxy ethylacetamide and the like.

When the polymerization reaction is conducted in the presence of the solvent, soluble linear or branched chain complex polymers and copolymers are obtained. By selection of a suitable solvent, crosslinking can be prevented even if there are present high concentrations of multi-funtional monomers.

The presence of the metal complex structure serves to inhibit the gelling of the reaction system. Therefore, higher concentration of the complex monomers can be used in the presence of the same amount of the cross linking monomer, than is possible in the case of the polymerization of the same but uncomplexed monomers.

If the polymerization reaction is carried out in the presence of a solvent for the complex monomers which solvent is not, however, a solvent for the resultant polymer and is a substance in which the resultant polymer also does not undergo swelling or swells only to a limited extent, then as the solubility decreases during the polymerization, the polymer formed begins to separate from the solution, the product formed being a macroreticular polymer. The properties of the latter macroporous polymers can by appropriate choice of the monomer, concentration of the monomer, the amount of crosslinking agent, the type of solvent and amount thereof used be varied substantially. When the amount of solvent used is increased above a certain or critical level, macrospherical particles predominantly having diameters of less than 1 micron are formed.

By conducting the polymerization in the substantially complete absence of any solvent, products are obtained constituting rigid macroporous polymer materials.

When the polymerization is carried out in the presence of a solvent which is effective for only partially swelling of the polymer, soft sponge-like polymer products are obtained. As is self evident, the degree of cross linking which takes place in the polymerization reaction also influences the properties of the resultant polymeric products.

The complex polymers and copolymers of the invention can also be prepared by carrying out the polymerization of the monomers per se in the presence of a solvent and of an aluminum salt. Thus, it has been found in accordance with the invention, that the complexing reaction can proceed simultaneously with the polymerization reaction resulting in the formation of the desired complex polymer. In order to successfully carry out the polymerization while simultaneously effecting the complexing reaction, a solvent must be selected which will not interfere with the desired reactions. In general, as solvent there is preferably used a hydrophilic substance such as water, alcohol, ketone, glycol, glycol ester or ether, amide, alkyl amide or the like. The presence of water is not required although it has been found that even traces of water act to accelerate the complex formation. The complex reaction of the monomers to form the complex polymers will take place quite satisfactorily using the aluminum salt, for example, aluminum chlorohydrol in the form of its suspension in an anhydrous alcohol.

A portion of the hydrophilic solvent can be replaced by an appropriate hydrophobic solvent, such as for example by an aromatic, aliphatic or halogenated hydrocarbon, ether, ester or the like.

This is particularly important in carrying out the copolymerization of the hydrophilic monomer with a hydrophobic monomer. In this latter case, the amount of the hydrophobic solvent required for maintaining the resultant polymer in solution can easily be established by the conventionally used empirical methods.

Thus in accordance with the invention the polymerization of the monomers can be carried out by bulk suspension and solution techniques. Polymerization in solution offers the advantage that higher concentrations of the monomers are thus made available for the polymerization reaction. Both types of polymers can be produced, i.e., soluble or insoluble crosslinked copolymers utilizing both the suspension and solution polymerization techniques.

In accordance with the invention, the complex polymers or copolymers can be prepared by another method based on utilizing polymers prepared in a first step by any of the conventional techniques known for their preparation and thereafter in a second step carrying out the complexing thereof with the metal salt using the same technique for complexing the polymer as described for complexing the monomer. The polymers can be linear or branched chain soluble polymers as well as crosslinked polymers. In the latter case, a suitable solvent must be provided for ensuring sufficient swelling of the three-dimensional polymer for the complexing to take place. This latter heterogeneous reaction generally takes place at a much slower rate than does the complexing conducted in solution.

Still another means is available for preparing the complex polymers and copolymers in cross-linked form in accordance with the invention and is based on the reaction mechanisms which are used in the synthesis of ion exchange resins and which involve employing in connection with the copolymers the well known ion exchange techniques for imparting to the copolymers the desired groups.

The polymerization reactions are initiated in the conventional manner and preferably by use of radical forming initiators. Instances of suitable initiators include dibenzoyl peroxide, tert. butyl peroctoate, cumene hydroperoxide, diazodilsobutyrodinitrille, diisopropylpercarbonate, ammonium persulfate, and the like, per se or in combination with a reducing agent, i.e., in the form of an oxidation-reduction system.

The solubility or swellability of the complex polymer or copolymer of the invention depends entirely on its chemical structure. The complexed hydroxyalkyl acrylate monomers are water-soluble while the corresponding methacrylates are water-insoluble but readily soluble in alcohol.

The copolymerization of the complex monomers results in a change in the solubility properties of the resulting copolymers. Thus, hydrophobic comonomers, such as the higher alkyl acrylates or methacrylates, styrene, vinyl acetate, vinyl benzoate and the like when present change the solubility characteristics so that the resultant copolymer is no longer soluble in alcohol but is soluble in benzene or in other hydrocarbons.

Hydrophilic comonomers such as acrylic or methacrylic acid, acrylamide or methacrylamide, quaternary ammonium monomers containing $SO_3H$ groups, esters of methacrylic acid esterified with propylene glycol trimethyl ammonium chloride, when present provide a copolymer which is soluble even in water.

In the case of carboxylic acid group containing polymers or copolymers, these are water-soluble following neutralization of the acid groups of the polymer.

When water-soluble polymer materials are desired, the above means for regulating the solubility characteristics can be kept in mind.

In accordance with a further aspect of the invention, the complex polymer still may be split so as to regenerate the original polymer. The complexed aluminum metal group is relatively stable. In those instances where the complex polymer is water-insoluble such as for example, the complexed 2-hydroxyethyl methacrylate polymer, the same can be subjected to precipitation in water, exhaustively washed with water and even boiled repeatedly with an excess of water without losing, i.e., giving up any of its aluminum content. The splitting of the polymer complex can however be readily accomplished by treatment thereof with acid or alkali. Thus, in accordance with the invention, it has been found that the use of dilute strong inorganic or organic acids, such as, hydrochloric acid, sulfuric acid, phosphoric acid, nitric acid or acetic acid, is effective to cause splitting of the complex without in any way adversely affecting the polymer material. The same results can be obtained by substituting alkalis for the acids.

The ability to split the complex provides an entirely new route for the preparation of hydrophilic polymer materials. As is well known, the majority of the hydrophilic monomers, for instance, 2-hydroxy methacrylate, 2- or 3-hydroxypropyl methacrylate and the like contain a small amount, i.e., 0.1–2% of the corresponding diester. The diester acts to bring about gelling, i.e., results in the formation of a three-dimensional polymer through cross-linking. As a result, even where the polymerization is carried out in solution the practical concentration of the starting monomers is for technical applications limited to from 10 to 15%. In the case of the aluminum complex, this is not the case, the complex being markedly effective to prevent such three-dimensional polymerization or cross-linking. The use of the aluminum complex allows for the solvent polymerization of hydrophilic monomers to be carried out with the monomer present in the solution in a concentration of 15–30% even though the monomers contain from 0.1 up to 2% of the diester.

It has further been found that the polymer complexes of the invention do not precipitate aluminum hydroxide upon neutralization even in those instances where the neutralization medium is one having a very high pH. Aluminum chlorohydrol precipitates out aluminum hydroxide following neutralization thereof with sodium hydroxide at a pH of 6.6. Most surprisingly and unexpectedly, the polymer complexes of the invention are able to withstand the effect of pH ranges of from 9 to 11 without any precipitation of aluminum hydroxide taking place. If the concentration of aluminum in the polymer solution is sufficiently high, approximately at least 2% (based on the concentration of aluminum oxide in the isolated polymer) the neutralization of such a polymer solution results at pH values in excess of 11 in the formation of a polymeric alcoholic gel.

The soluble complex polymers or copolymers can also in accordance with the invention be subsequently cross-linked. The simplest method for carrying out such cross-linking is heat curing which brings about a reaction of the pending double bonds which are present creating a three-dimensional polymeric network. A portion of this network is also cross-linked by the reaction of the OH groups which are present to form ether linkages by hydration. Chemical cross-linking utilizing reactive bi- or polyfunctional compounds, i.e., diesters, diisocyanates, diepoxides, vinylaziridinyl compounds and the like, can also be carried out and there is thereby provided an extremely broad range of alternatives for the cross-linking and for varying the properties of the resultant cross-linked polymers.

The complex polymers of the invention containing aluminum, zinc or zirconium metal in complex bound form can be used most advantageously for entrapping, encapsulating active agents such as medicaments, fragrances, insecticides, herbicides, pesticides, anti-bacterial, antimicrobial, plant growth promoting and like substances. The complex copolymers are particularly suitable for use in the preparation of such active agents where a sustained release effect is desired. They can also be used where instantaneous release is desired, i.e., whereby application of a suitable solvent or like substance for the complex copolymer all of the active agent is made available. Further by suitable choice of the formulation both as to complex copolymer and active agent a differential entrapment may be realized.

Illustrative of the various formulations possible are the incorporation of an antiperspirant such as aluminum chlorohydrol, a pesticide such as thuramidsulfide, a medicinal such as phenoxymethyl penicillin antibiotic, a flavoring or sweetening agent such as natural anise flavor, a fragrance such as oil of orchids perfume essence and the like.

As the basic polymer or copolymer used for complexing the metal can be considerably varied through the extremely broad range of synthesis possibilities by which they can be prepared, i.e., complex polymers and copolymers containing different functional groups both hydrophobic and hydrophilic with resultant large variations in the degree of adhesion of the resultant polymer films to the skin and other substrates are made available in accordance with the invention.

By varying the basic structure of the polymer as for instance by varying its hydrophilic or hydrophobic nature or alternatively by varying the degree of cross-linking and branching in the polymer, sustained release and long-lasting as well as more or less instantaneous release action compositions are now made possible.

The complex polymer and active agent can be formulated as solutions, sprays and the like for application thereof to various surfaces including plastic, paper, glass, wood, skin and the like.

It is also possible to prepare the polymers and polymer complexes in the form of foams, for instance as friable polymeric foams which can thereafter be ground to fine powders. In this connection the conventional foaming agents can be used which will not interfere with the complex formation. An instance of a preferred foaming agent is diazobutyrodinitrile which has the advantage that it can also be used as an initiator for the polymerization.

The following examples are given in order to more fully illustrate the invention, the same are, however, in nowise to be construed as a limitation of the scope thereof.

EXAMPLE 1

Gel

26 Grams monomeric 2-hydroxyethyl methacrylate containing 0.5% diester were mixed with 11 grams of dry aluminum chlorohydrol and the resultant mixture heated in an open vessel at 120°C for 2 hours. The solid material present consisting of undissolved aluminum salt was filtered off. There was added to 10 ml of the filtered monomeric solution 0.05 ml of tert. butyl peroctoate initiator and polymerization carried out under nitrogen at 80°C. After 15 minutes a cross-linked gel of aluminum complex polymer was formed. The aluminum content thereof amounted to 0.07%. The swelling of the gel amounted to 0.4 g of water per gram of dry polymer.

The same procedure was followed for preparing gels on the basis of 2- or 3-hydroxypropylmonomethacrylate, diethylene glycol monomethacrylate, glycerine monomethacrylate and similar hydroxy group containing monomers.

When in place of the aluminum chlorohydrol, aluminum bromohydrol and aluminum sulphamate were used similar results were obtained.

EXAMPLE 2

Gel

The same procedure as set out in Example 1 was followed for complexing monomers with aluminum salts in the presence of water. 26 Grams of monomeric 2-hydroxyethyl methacrylate containing 0.5% diester were mixed together with 5 grams of 50% aluminum chlorohydrol solution and the solution thusly obtained heated in a closed vessel at 100°C for 2 hours. The resulting clear solution was polymerized to a three-dimensional gel at 80°C, as described in Example 1.

The Example was repeated using amounts of aluminum chlorohydrol solution varying from 0.1 up to 22g. In each case the polymerization produced cross-linked gels containing complex-bound aluminum.

When the aluminum chlorohydrol was replaced by aluminum bromohydrol, aluminum sulphamate and other salts disclosed as suitable for use in the process of the invention, similar results were obtained.

EXAMPLE 3

Sponge

30 Grams of a complex aluminum containing hydroxyethyl methacrylate monomer prepared according to Examples 1 or 2 were diluted with 45 ml of 10% ammonium persulfate solution. Following heating thereof at 70°C, a cross-linked macroporous, soft, sponge-like polymer was formed.

The amount of water present in the system was varied from 50 up to 90% and sponge-like polymers having an increasing porosity resulted.

When the initiator system was changed by replacing the ammonium persulfate with dibenzoyl perxoide, t. butyl peroctoate, diisopropylpercarbonate or an oxidation/reduction system which as dibenzoylperoxide-dimethylaminoethylacetate, equally successful results were obtained.

EXAMPLE 4

30 Grams of complexed hydroxyethyl methacrylate monomer prepared according to Example 1, 12.5 grams of 60% technical diveinylbenzene (20% of cross-linking) and 0.4 grams of dibenzoyl peroxide were dissolved in 13 ml of toluene. Nitrogen was bubbled through the resulting solution and the polymerization carried out in a closed polypropylene vessel at 50°C for 8 hours. A solid macroporous hard polymer was obtained.

When the Example was repeated varying the content of divinylbenzene from 2 to 60% calculated at 100% substance for cross-linking, there were obtained sponge-like polymers swellable in water having between 2 to 10% of cross-linking. When the cross-linking amounted to more than 10% and specifically from 10% to 60% hard, brittle polymers having an internal pore area of from 50 to 150, m²/g were obtained.

An increase in the amount of toluene of up to 15% by volume resulted in almost no macroporosity in the polymer but in amounts above that i.e., up to 50% hard macroporous polymers resulted. If the amount of toluene is increased to above 50% a polymeric cross-linked powder having particle size of less than 1 micron, was obtained.

The toluene could be replaced by other solvents suitable for effecting precipitation of the polymer but constituting a solvent for the monomers such as ethylacetate, dibutylphthalate and the like.

When the divinylbenzene was replaced by ethylene glycol bismethacrylate, methylenebisacrylamide or other similar cross-linking agents, similar results were obtained.

EXAMPLE 5

Solvent Polymerization 12.45 g Of technical hydroxypropyl methacrylate containing 2% of diester were dissolved in 63.5 g of ethylalcohol and 25 g of water. 0.05 g Of aluminum chlorohydrol dissolved in 0.15 ml of water were then added. Nitrogen was bubbled through the system in a pressure vessel and polymerization initiated by 0.12 ml of tertiary butylperoctoate. The polymerization was carried out at 85°C for 12 hours. After cooling, the polymer was isolated by precipitation in ether. On analysis, the polymer contained 0.03% of aluminum oxide.

The same procedure was used but the polymerization was carried out with varying molar proportions of aluminum chlorohydrol and hydroxypropyl methacrylate as shown in the following Table:

| Hydroxypropyl-methacrylate mol | Alum. Chloro-hydrol mol: | % of alum. Theory: | Oxide in Polymer Found: |
|---|---|---|---|
| 0.99 | 0.01 | 0.185 | 0.0375 |
| 0.9 | 0.1 | 0.945 | 0.882 |
| 0.8 | 0.2 | 5.95 | 6.57 |
| 0.7 | 0.3 | 5.93 | 9.01 |
| 0.6 | 0.4 | 13.05 | 12.04 |
| 0.5 | 0.5 | 17.3 | 21.8 |

EXAMPLE 6

Solvent Polymerization 24.84 g Of 2-hydroxyethyl methacrylate containing 0.5% of diester were dissolved in 80 g of ethylalcohol and 20 g of water and mixed with 0.16 g of aluminum chlorohydrol dissolved in 0.5 ml of water. Nitrogen was bubbled through the solution and 0.25 ml of tert. butyl peroctoate added thereto.

Polymerization was carried out for 8 hours in a pressure vessel at 85°C. The polymer thereby formed was isolated by precipitation in ether. The content of aluminum oxide therein was determined and amounted to 0.336%.

The identical procedure was carried out using varying molar proportions of hydroxyethyl methacrylate and aluminum chlorhydrol.

| Molar proportions Hydroxyethylmethacrylate mol | % Aluminum oxide in polymer | | |
|---|---|---|---|
| | Alum. chloro-hydrol mol: | Theory: | Found: |
| 0.99 | 0.01 | 0.298 | 0.30 |
| 0.9 | 0.1 | 3.11 | 3.52 |
| 0.8 | 0.2 | 6.52 | 7.38 |
| 0.7 | 0.3 | 8.62 | 10.67 |
| 0.6 | 0.4 | 13.45 | 13.9 |

The solution of the polymeric complexes could be neutralized with sodium hydroxide up to a pH of 9–11 without precipitation of aluminum hydroxide occurring.

EXAMPLE 7

23.7 g Of 2-hydroxyethyl methacrylate and 6.3 g of aluminum bromohydrol were dissolved in 48 g of water and 112 g of ethyl-alcohol and nitrogen bubbled through the resulting solution. 0.4 ml Of tert. butyl peroctoate were then added and the solution heated to 85°–90°C under pressure for 24 hours. The solution of the complex polymer thereby obtained was clear and yellowish in color.

EXAMPLE 3

17.18 g Of 2-hydroxyethyl methacrylate, 2.82 g of methacrylic acid, 37 g of water and 135 g of ethylalcohol were mixed with 3.4 g of aluminum chlorohydrol and 0.2 ml of tert. butyl peroctoate. Polymerization was carried out at 82°C for 10 hours under pressure. The polymerization solution obtained was clear and could be neutralized with sodium hydroxide up to a pH of 10.5 without precipitation of aluminum hydroxide.

The same procedure was thereafter carried out for copolymerizing and complexing of acrylic and itaconic acid.

EXAMPLE 9

14.6 g Of hydroxyethyl methacrylate, 5.4 g of vinyl pyrrolidone and 5.76 ml of aluminum chlorohydrol solution containing 0.3 g of aluminum chlorohydrol per ml were dissolved in 41 ml of water and 135 g of ethylalcohol. The polymerization was initiated with 0.2 ml of tert. butyl peroctoate and was carried out in a pressure vessel at 81°–83°C for 8 hours. The resulting clear solution of the complex polymer did not precipitate aluminum hydroxide until a pH of 11 had been reached.

EXAMPLE 10

10.4 g Of hydroxyethyl methacrylate, 6.25 g of dimethylaminoethyl methacrylate, 3.43 g of methacrylic acid and 1.1 ml of aluminum chlorohydrol solution containing 0.3 g of aluminum chlorohydrol per ml were dissolved in 37 ml of water and 135 g of ethylalcohol. Following the addition of 0.2 ml of tert. butyl peroctoate nitrogen was bubbled through the reaction solution and it was heated in a closed vessel at 81°–83°C for 8 hours. A clear solution of complex aluminum containing terpolymer was obtained. When the amount of aluminum chlorohydrol used was ten fold that just set out a cross-linked gel was formed.

EXAMPLE 11

40 g Of 2-hydroxyethyl methacrylate monomer were dissolved in 160 g of absolute ethylalcohol. 0.2 g Of dry aluminum chlorohydrol and 0.41 ml tertiarybutyl peroctoate were then added to the resulting solution. The reaction mixture was flushed with nitrogen and heated in a closed vessel at 80°–85°C for 20 hours. Any undissolved aluminum salt present was removed by filtering.

The polymer solution thereby obtained contained 19.5% of solids.

The complex polymer was isolated by precipitation in ether. Its aluminum oxide content amounted to 0.31%.

EXAMPLE 12

141.5 g of laurylmethacrylate (60 molar %), 108.5 g of 2-hydroxyethyl methacrylate and 2.44 ml of aluminum chlorohydrol solution (concentration 0.3 g/ml were dissolved in 1000 g of ethyl alcohol in a glass-lined autoclave. 2.5 ml of tertiary-butylperoctoate were then added and the solution bubbled through with nitrogen. The autoclave was then sealed and polymerization carried out at 82°–85°C. for 8 hours. The polymerization solution which was obtained was clear.

The same procedure was repeated but with varying molar ratios of lauryl methacrylate and hydroxyethyl methacrylate. The molar percentages of lauryl methacrylate amounted to 0.5–60%.

In addition the procedure was repeated using in place of the lauryl methacrylate, methyl methacrylate, butyl methacrylate, isobornyl methacrylate, isodecyl methacrylate, tridecyl methacrylate, styrene, vinyl acetate and acrylonitrile in amounts of up to 60 molar percent.

Above a 60% molar percentage, methylethylketone, benzene, toluene or a similar solvent singly or in admixture had to be added in order to retain the polymer in solution.

EXAMPLE 13

Neutralization 23.33 g OF 2-hydroxyethyl methacrylate were dissolved in 80 g of ethylalcohol and 20 g of water. 1.67 g of aluminum chlorohydrol were then added. The polymerization was initiated by addition of 0.23 ml of diazodiisobutyrodinitrile. Nitrogen was bubbled through the polymerization solution, the pressure vessel then sealed and heated under stirring at 85°C for 8 hours.

A clear solution of the complex polymer ws thereby obtained. The aluminum oxide content of the complex polymer which had been isolated by precipitation amounted to 3.5%.

A sample of the solution of the complex polymer having a pH of 3.0 was titrated with 1 N sodium hydroxide. No precipitation of aluminum hydroxide occurred until a pH of 9.5 had been reached. A polymer prepared in an analogous manner and containing only 0.3% of aluminum oxide did not precipitate aluminum hydroxide upon neutralization until a pH of 11.2 had been reached.

EXAMPLE 14

Stability of the Complex

A sample of the complex polymer prepared according to the procedure of Example 2 was isolated by precipitation in ether. The aluminum oxide content thereof was found to be 0.30%.

2 g Of this dry polymer were swollen in water and washed exhaustively with excess of water (5000 ml) over a period of 4 days. The aluminum oxide content following washing amounted to 0.32%.

5 g Of this ether isolated polymer were dissolved in 50 ml of 70% ethylalcohol, the polymeric solution poured into 500 ml of water and the reprecipitated polymer washed continuously with 5000 ml of water for 3 days. The aluminum oxide content of the thusly reprecipitated and washed polymer amounted to 0.29%.

100 ml Sample of a solution of a complex polymer the original aluminum oxide content of which after ether isolation amounted to 0.167% was poured into 1000 ml of 5% ammonium chloride solution. The polymer was then precipitated and washed exhaustively with 5000 ml of water for 20 hours. The aluminum oxide content of the polymer was determined after such washing and amounted to 0.165%.

10 g Of the thusly isolated polymer were dissolved in 200 ml of 80% ethylalcohol, precipitated out in 1000 ml of water and the polymer washed with 5000 ml of water over a 3 day period. The aluminum content of this washed polymer amounted to 0.163%.

2 g Of this polymer were boiled in 100 ml of water for 15 minutes and thereafter washed with 1000 ml of water. The aluminum oxide content of the boiled and washed polymer amounted to 0.166%. This procedure was repeated five times, the aluminum oxide content following the fifth boiling was determined and amounted to 0.161%.

When the boiling was repeated for a total of 10 times, the aluminum oxide content amounted to 0.158%.

It is clear from this Example that the aluminum complex is very securely bound to the macromolecule, resisting redissolving, reprecipitation and even repeated boiling in water.

EXAMPLE 15

100 g Of the polymer prepared and isolated according to the procedure of Example 6 and containing 3.52% of aluminum oxide were dissolved in 900 ml of 70% ethylalcohol. The resulting solution was acidified with 20 ml of concentrated 37% hydrochloric acid and stirred for 1 hour at room temperature. The solution was then poured into 5000 ml of water, the precipitated polymer which formed was washed with water to neutrality and dried at room temperature. 90 g of poly-(2-hydroxyethyl methacrylate) without any trace of aluminum were recovered.

EXAMPLE 16

50 ml Of a solution of 2-hydroxyethyl methacrylate complex polymer prepared according to Example 6 and containing 0.385% $Al_2O_3$ and having a solids content of 0.170 g/ml were mixed with 8.4 g of rose oil. The clear solution which was thereby formed could be deposited out in the form of a dry film which did not exhibit syneresis of the fragrant oil. The film could be used as such or after grinding could be used in the form of a powder. A long lasting fragrance releasing effect was obtained in either case.

In place of the above-named polymer, copolymers prepared according to Examples 7, 8, 9, 10, 11 and 12 could be advantageously used for entrapping the rose oil as well as other combinations of perfumes, colognes, floral fragrances, odor counteractants and the like as well as flavors such as anise, peppermint, vanilla, rum and the like.

EXAMPLE 17

26 g Of 2-hydroxyethyl methacrylate prepared as set out in Example 2 in the presence of 25 g of rose oil and 5 g of aluminum chlorohydrol resulted in the formation of a clear gel containing entrapped therein the rose oil. After pulverizing or grinding the polymeric material thus obtained a long lasting perfume powder was recovered.

In the same manner, other copolymers and different perfumes and/or flavors could be utilized to form long lasting sustained release fragrant and/or flavored products.

EXAMPLE 18

40 g Of 2-hydroxyethyl methacrylate, 60 g of water and 40 g of citronella oil were mixed to ether and the mixture emulsified with the help of 0.1 g of a non-ionic emulsifier such as alkyl phenol polyglycolester. 0.4 ml of tert. butylperoctoate were added and the resulting emulsion polymerized at 80°C for 15 minutes. A sponge-like polymer containing the rose oil was thereby obtained. The polymer was ground up to form a sustained release perfume powder material.

EXAMPLE 19

The procedure of Example 18 was repeated using as initiator for the reaction diazodiisobutyrodinitrile. 1.0 g of a foamed polymer product was obtained which was further worked up as set out in Example 18.

EXAMPLE 20

An antiperspirant pad containing a polymer complex carrier and aluminum chlorohydrol as the active ingredient was prepared as follows.

A thin (1 mm) polyurethane foam sheet 18 × 25 cm was soaked in an alcoholic solution of the polymer complex prepared as in either Example 5 or 6 containing 50 mol percent of aluminum chlorohydrol. Excess liquid was drained therefrom and the foam was dried. The sheet was cut into square pieces 5 × 5 cm. Pads containing 0.1–0.3 g of aluminum chlorohydrol were obtained. Upon wetting with water, the pad was suitable to be used as single use antiperspirant device.

To increase the amount of aluminum chlorohydrol in the pad, the polyurethane foam was first saturated with aluminum chlorohydrol powder and subsequently sprayed with a polymer complex solution, prepared according to Examples 5 or 6, containing 10 mol percent of aluminum chlorohydrol. After drying, pads were obtained in which aluminum chlorohydrol was firmly entrapped and did not powder out. In this way, the amount of aluminum chlorohydrol was increased to 0.3–0.5 g per 5 × 5 cm pad.

To prepare softer pads, dipropylene glycol was added to the spraying solution in amounts of 50, 60, and 100 percent, based on the polymer solids.

Aluminum chlorohydrol could be successfully replaced by $AlCl_3.6H_2O$.

EXAMPLE 21

An applicator for hair dye was prepared as follows:

5 g of a polymer complex solution containing 10 mol percent of aluminum chlorohydrol, prepared according to Examples 5 or 6, was mixed with 0.5 g of commercial hair dye (Clairol 775), poured into a polyurethane foam cube, and dried. After soaking in water, slow release of the hair dye was achieved.

EXAMPLE 22

Carrier films of a polymer complex containing an entrapped disinfectant were prepared as follows:

10 ml portions of a solution of a complex polymer, prepared according to Examples 5 or 6 and containing 1 mol percent of aluminum chlorohydrol, said solution containing 0.07 g solids/ml, were mixed with alkyl dimethyl benzyl ammonium chloride in amounts such that the ratios by weight of disinfectant to polymer solids in the resulting solutions were, respectively, 25:75, 40:60, 50:50, and 60:40.

Films were cast from the solutions.

After drying, films containing entrapped quaternary disinfectant were obtained. At ratios up to 50:50, the films were hard and non-tacky.

The solutions were also incorporated into cellulose or polyurethane sponges and dried. Slow release disinfectant sponges were obtained.

EXAMPLE 23

Various fragrance-releasing articles and compositions were prepared as follows:

Various commercial fragrances were mixed with a solution of polymer complex prepared according to Examples 5, 6, or 12 to contain 1 mol percent of aluminum chlorohydrol. The ratio of polymer solids to fragrance was 50:50. The fragrances used were "Jean Naté" and "Ritual" (Charles Lanvin of the Ritz), Lemon Bouquet 138 (Lautier & Fils) and essential oil Citronella Ceylon.

Dry cellulose sponge cubes weighing 2 g each were soaked in the solution of the fragrance and polymer. 4–5 g of the solution were retained in each cube. The cubes were air-dried and released the perfume over a period of 1–2 months.

Porous ceramic tiles were soaked in the same solutions. The release of fragrance was slow and could be accelerated by soaking the tiles in water.

Aerosol formulations of the fragrances were also prepared as follows:

| | |
|---|---|
| Polymer complex | 5 g |
| Ethyl alcohol | 70 g |
| Propylene glycol | 2 g |
| Fragrance | 2 g |
| Freon F-12 | 21 g |

Similar formulations were also effective as underarm deodorants and antiperspirants, foot sprays, or as mixtures with talcum powder.

EXAMPLE 24

Various pesticidal films employing polymer complexes as carriers were prepared as follows. Copolymers prepared according to Example 12 are preferably used.

Pyrethrins or pyrethroids (which may be pure solids or solutions in kerosene) were mixed with solutions of copolymers in a 50:50 weight ratio of polymer and pyrethrin solids. Films were cast and examined. The copolymers comprised 2-hydroxyethyl methacrylate and various comonomers in the mol percentages indicated in the following Table, complexed with 5 mol percent of aluminum chlorohydrol.

TABLE

| Comonomer | Mol % | Film Quality |
|---|---|---|
| None | (0) | Droplets of liquid separate in the film |
| Ethyl hexyl acrylate | 50 | Droplets of liquid separate in the film |
| Butylmethacrylate | 30 | Separates |
| Stearyl methacrylate | 50 | Homogeneous film |
| Stearyl methacrylate | 40 | Homogeneous film, tacky |
| Stearyl methacrylate | 20 | Homogeneous film, non-tacky |
| Lauryl methacrylate | 40 | Homogeneous film |
| Lauryl methacrylate | 30 | Homogeneous film |
| Lauryl methacrylate | 10 | Homogeneous film |
| t-octyl acrylamide | 50 | Homogeneous film, non-tacky |
| t-octyl acrylamide | 40 | Homogeneous film, non-tacky |
| t-octyl acrylamide | 30 | Homogeneous film, non-tacky |
| Ethoxyethyl methacrylate | 20 | Homogeneous film |

The solutions containing hydrophobic comonomers in proper ratios gave homogeneous films and also could be easily incorporated into aerosol formulations.

Similarly, d-trans-allethrin, piperonyl butoxide, synthetic pyrethrins i.e. pyrethroids [for example (5-benzyl-3-furyl)-methyl-2,2-dimethyl-3-(2-methyl-propenyl cyclopropane)-carboxylate] were entrapped with identical results.

EXAMPLE 25

Compositions containing copolymers prepared as in Example 12 as a carrier matrix and a fragrance as the active ingredient were tested for adhesion on polyethylene and polypropylene substrates.

Rose oil (Bellmay No. 940) was added to the copolymer solutions in an amount by weight equal to the polymer solids. Films were cast on polypropylene and polyethylene and adhesion and odor value were evaluated. The copolymers comprised 2-hydroxyethylmethacrylate and the comonomers listed in the following Table, complexed with 1 mol percent of aluminum chlorohydrol.

TABLE

| Comonomer | Mol Percent | Adhesion after 2 Weeks | Odor Value after 2 Weeks |
|---|---|---|---|
| Butyl methacrylate | 30 | — | — |
| Ethyl hexyl methacrylate | 50 | -+ | + |
| Ethyl hexyl methacrylate | 60 | -+ | + |
| Ethyl hexyl methacrylate | 70 | -+ | + |
| Ethyl hexyl methacrylate | 80 | -+ | + |
| Lauryl methacrylate | 40 | -+ | + |
| Lauryl methacrylate | 30 | - | + |
| Stearyl methacrylate | 50 | -+(tacky) | + |
| Stearyl methacrylate | 40 | -+ | + |
| Stearyl methacrylate | 30 | -+ | + |
| Ethoxyethyl methacrylate | 60 | -+ | + |
| Ethoxyethyl methacrylate | 50 | + | + |
| t-octyl acrylamide | 30 | - | + |
| Vinylidene chloride | 30 | - | + |

Odor Value: —= loss += acceptable
Adhesion: —= peels off +—= starts to peel += good ++= very good Plastic flowers (polyethylene or polypropylene) were coated with various of the polymer-fragrance solutions using a spray gun or aerosol formulation. Odor effects lasting up to three months were achieved.

EXAMPLE 26

The technique of Example 25 was used to coat a wax substrate with perfumed copolymer films.

The perfume used was Lavender 55524 (Fritsche D & 0) in an amount equal to the weight of the solids in the polymer solutions. The compositions of the copolymers were 50, 60, and 80 mol percent of 2-hydroxyethylmethacrylate and, respectively, 50, 40, and 20 mol percent of stearyl methacrylate containing 1 mol percent of complexed aluminum chlorohydrol.

Candles and wax figurines were coated with these solutions leaving long-lasting perfumed surfaces even after six months.

EXAMPLE 27

Compositions suitable as a cosmetic sunscreen were prepared as follows:

Solutions of copolymers of 2-hydroxymethylmethacrylate with, respectively, 10, 20, and 30 mol percent of lauryl methacrylate, each containing 5 mol percent of aluminum chlorohydrol (cf. Example 12) were used to entrap amyl-p-amino benzoate in amounts up to 20 percent by weight of total solids.

On drying, transparent non-tacky films were obtained.

EXAMPLE 28

Films containing a volatile insect repellant were prepared as follows:

o,o-dimethyl-2,2-dichlorovinyl phosphate (DDVP — "Vapona") was incorporated into polymeric films using polymers and copolymers prepared according to Examples 6 and 12. The amount of DDVP was 50 percent of total solids. Aluminum complexed polymers comprising 2-hydroxyethylmethacrylate with 10 mol percent of aluminum chlorohydrol and various comonomers were used. The following compositions were tested.

TABLE

| Comonomer | Mol % | DDVP % | Film Quality |
|---|---|---|---|
| None | (0) | 50 | Tacky |
| None | (0) | 30 | Dry |
| None | (0) | 10 | Dry |
| Stearyl methacrylate | 20 | 50 | Tacky, clear |
| Stearyl methacrylate | 20 | 30 | Dry, clear |
| Stearyl methacrylate | 40 | 50 | Waxy, clear |
| Stearyl methacrylate | 40 | 30 | Dry, clear |
| Stearyl methacrylate | 50 | 50 | Dry |
| Stearyl methacrylate | 50 | 30 | Dry |
| Ethoxyethyl methacrylate | 30 | 50 | Tacky |
| Ethoxyethyl methacrylate | 30 | 30 | Dry |
| Methylmethacrylate | 20 | 50 | Tacky |
| Methylmethacrylate | 20 | 30 | Dry |
| Lauryl methacrylate | 30 | 50 | Tacky |
| Lauryl methacrylate | 30 | 30 | Tacky |
| Lauryl methacrylate | 10 | 50 | Tacky |
| Lauryl methacrylate | 10 | 30 | Dry |

Films exhibiting long-lasting DDVP activity were obtained.

EXAMPLE 29

Mosquito repellant, N,N-diethyl-m-toluamide, was entrapped in polymeric films. A copolymer of lauryl methacrylate (20 mol percent) and 2-hydroxyethylmethacrylate (80 mol percent) complexed with 1 mol percent of aluminum chlorohydrol, prepared according to Example 12, was used.

50 percent of N,N-diethyl-m-toluamide, by weight of total solids, was incorporated into dry polymeric films.

The same copolymers were also suitable for entrapment of toluamide, sunscreens, and tanning oils simultaneously.

EXAMPLE 30

Panty hose were coated with a polymer-entrapped fragrance as follows:

Solutions of copolymers containing 30 or 40 mol percent of lauryl methacrylate and 70 or 60 percent of 2-hydroxyethylmethacrylate complexed with 1 mol percent of aluminum chlorohydrol, prepared according to Example 12, were mixed with 50 percent of "Floral Arpeie" fragrance (Bellmay, No. 67) and sprayed on nylon panty hose. Cold detergent washing tests were performed. In both cases if a heavy or medium coating was applied, 10 washing cycles were possible before the fragrance note disappeared. Even four to five cycles were possible with very thin coatings.

EXAMPLE 31

To counteract odor, diapers were coated with a fragrance and polymer. The fragrance was released on contact with water.

A polymer complex solution, prepared according to Examples 5 or 6 and containing 10 mol percent of complexed aluminum chlorohydrol, was mixed with an "odor counteractant composition for diapers" (Airwick Industries, Inc., No. 1487) in a ratio of counteractant:polymer solids of 60:40. The solution was diluted with alcohol and sprayed on diapers, the absolute quantity of the counteractant being 0.1 g per diaper. After drying, the scent of the odor counteractant disappeared but could be re-developed by moistening the diaper even after 3 weeks' exposure to ambient temperatures without packaging.

EXAMPLE 32

Complex polymers prepared according to Examples 5 or 6 and containing 1 mol percent of complexed aluminum chlorohydrol were used to entrap and slowly release a commercial liquid body soap ("Xanadu", Fabergé).

99 ml of the liquid body soap were mixed with 1000 ml of an alcoholic solution of the complexed polymer (1 ml contains 0.099 g of polymer solids).

Cellulose sponges were impregnated with this solution and dried at 50°C. The average content of the body soap in the dried sponges was 0.04–0.07 g per cc. A sponge having a total volume 40 cc released the soap even after 100 cycles of repeated squeezing and rinsing with tap water.

Similarly, lauryl sarcosinate was entrapped in the same polymer or in other copolymers according to Example 12 in a weight ratio of 50:50 with the polymer solids in the solution.

EXAMPLE 33

Para-amino benzoic acid (PABA) is a very effective sunscreen but its solutions are staining when applied to the skin.

Complex polymers prepared according to Example 12 were used to entrap PABA to give clear, non-staining films. Copolymers of 2-hydroxyethylmethacrylate and hydroxypropylmethacrylate complexed with 1 mol percent of aluminum chlorohydrol were used. The comonomers and the amount of PABA was varied as in the following Table.

TABLE

| Comonomer | Mol % | PABA (Percent of Total Solids) | Film Quality |
|---|---|---|---|
| Lauryl methacrylate | 40 | 50 | Crystallizes |
| Lauryl methacrylate | 40 | 40 | Crystallizes |
| Lauryl methacrylate | 40 | 20 | Crystallizes |
| Lauryl methacrylate | 40 | 10 | Clear |
| t-octyl acrylamide | 40 | 50 | Crystallizes |
| t-octyl acrylamide | 40 | 20 | Clear |
| t-octyl acrylamide | 40 | 10 | Clear |
| t-octyl acrylamide | 40 | 5 | Clear |
| Ethoxyethyl methacrylate | 50 | 20 | Clear |

TABLE-continued

| Comonomer | Mol % | PABA (Percent of Total Solids) | Film Quality |
| --- | --- | --- | --- |
| Ethoxyethyl methacrylate | 50 | 10 | Clear |
| Ethoxyethyl methacrylate | 50 | 5 | Clear |

Since the usual content of PABA sunscreen in a film does not exceed 5 percent in practice, entrapment in all of the polymeric systems tested would be satisfactory. All films after drying were non-staining even after repeated wetting with water.

EXAMPLE 34

Dihydroxy acteone (DHA) is an oxidative tanning agent turning the color of the skin to brown. However, this process takes from 6–8 hours while the color of the skin first changes to yellow before turning brown.

Cosmetic bronzing compositions containing DHA, a bronze dye, and a polymeric carrier which excludes the DHA on drying, were prepared as follows:

20 ml of an alcoholic solution of an 80:20 (mol percent) copolymer of 2-hydroxyethylmethacrylate and lauryl methacrylate, complexed with 1 mol percent of aluminum chlorohydrol (1 ml contains 0.156 g of polymer solids) were mixed with 31 ml of a solution of DHA in 93 percent ethyl alcohol (1 ml contains 0.1 g of DHA) and 30 ml of a brown dye ("Irgacet Brown 2GL", Clairol).

On application to the skin and drying, an adherent, water-resistant, non-staining film entrapping the dye, but from which DHA is excluded (and hence made available for skin reaction), was formed. After 6–8 hours, the bronze dye film can be removed with soap and water to reveal the tanning caused by DHA.

Copolymers comprising 95–60 mol percent of 2-hydroxymethyl methacrylate and 5–40 mol percent of lauryl methacrylate, each complexed with 1 mol percent of aluminum chlorohydrol and prepared according to Example 12, can be used to compound similar preparations.

EXAMPLE 35

Polymer carriers can be used to entrap oils such as bath oil.

Namely, 10 ml of a polymer complex prepared according to Examples 5 or 6 (1 ml contains 0.160 g) were mixed with 1.6 g of "Swedish Bath Oil" (Clairol — mainly pure mineral oil) and the solution was poured onto cellulose or polyurethane sponges. After drying, the sponges slowly released the bath oil on contact with water.

Similarly, the bath oil was replaced by isopropyl myristate. When a part of the 2-hydroxyethylmethacrylate is replaced by lauryl methacrylate (for example, 90 mol percent of 2-hydroxyethylmethacrylate and 10 mol percent of lauryl methacrylate), the release of the oil is much slower.

EXAMPLE 36

Topical medicaments, e.g. analgesics and rubifacients, can be incorporated into polymer carrier films.

Thus, 20 g of methyl salicylate and 8 g of acetulan (acetylated lanolin alcohol) were mixed with a copolymer of lauryl methacrylate and 2-hydroxyethyl methacrylate (80:20 mol percent), complexed with 1 mol percent of aluminum chlorohydrol, in 265.5 g of ethyl alcohol.

When applied to the skin, non-tacky, homogeneous films exhibiting prolonged release of the methyl salicylate were formed.

The lauryl methacrylate can be replaced with, for example, 20 mol percent of stearyl methacrylate or 30 mol percent of isobornyl methacrylate, with similar results.

Similarly, benzocaine was incorporated as a topical anesthetic into polymer carriers as described in this Example.

What is claimed is:

1. A composition comprising an effective amount of an active ingredient dispersed in a polymer complex consisting essentially of (1) a polymer which is a homopolymer or copolymer comprising a monomer having a hydrophilic functional group and (2) from 0.1 to 90 mol percent based on the hydrophilic functional groups present in said homopolymer or copolymer, of aluminum, zinc, or zirconium metal bound in complex form, said monomer being selected from the group consisting of hydroxyalkyl esters of $\alpha,\beta$-unsaturated carboxylic acids and ethylenically unsaturated monomers containing an amino group, said copolymers further comprising from 0.5 to 60 mol percent of an ethylenically unsaturated monomer free of said hydrophilic functional groups.

2. A composition as in claim 1 wherein said polymer is a polymer or copolymer of an hydroxyalkyl ester of an $\alpha,\beta$-unsaturated carboxylic acid.

3. A composition as in claim 1 wherein said polymer is a polymer or copolymer of an hydroxyalkyl acrylate or methacrylate.

4. A composition as in claim 1 wherein said complex bound metal is aluminum.

5. A composition as in claim 1 wherein said active ingredient is a cosmetic agent.

6. A composition as in claim 1 wherein said active ingredient is a fragrance.

7. A composition as in claim 1 wherein said active ingredient is a disinfectant.

8. A composition as in claim 1 wherein said active ingredient is a pesticide or insect repellant.

9. A composition as in claim 1 wherein said active ingredient is an antiperspirant.

10. A composition as in claim 1 wherein said active agent is a sunscreen.

11. A composition as in claim 1 wherein said active agent is a surface-active agent.

12. A composition as in claim 1 wherein said active agent is a topical anesthetic.

* * * * *